United States Patent [19]

Sakschek

[11] Patent Number: 4,609,245
[45] Date of Patent: Sep. 2, 1986

[54] DISPENSER AND METHOD FOR DISPENSING HUNTING ODORS

[76] Inventor: Helmut W. Sakschek, 618 Fairview Ave., Neenah, Wis. 54956

[21] Appl. No.: 766,676

[22] Filed: Aug. 16, 1985

Related U.S. Application Data

[63] Continuation of Ser. No. 674,468, Nov. 21, 1984, abandoned, which is a continuation of Ser. No. 413,080, Aug. 30, 1982, abandoned.

[51] Int. Cl.$^4$ .................. A01N 25/00; A61L 9/04
[52] U.S. Cl. .................. 239/36; 239/44; 239/55; 43/1; 43/2; 401/131; 401/199
[58] Field of Search .................. 222/1, 3, 175, 187, 222/192; 239/36, 37, 42-44, 47, 49, 53-57, 34, 60, 211, 145, 152; 261/104, DIG. 17; 401/195, 52, 131, 198, 199; 312/31.04; 43/2, 42.06, 44.99

[56] References Cited

U.S. PATENT DOCUMENTS

| | | | |
|---|---|---|---|
| 2,503,080 | 4/1950 | Tefft et al. | 401/67 |
| 2,959,354 | 11/1960 | Beck | 239/36 |
| 3,046,192 | 7/1962 | Bilyeu | 239/56 X |
| 3,446,563 | 5/1969 | Burnham | 401/199 |
| 3,767,520 | 10/1973 | Dick et al. | 401/198 X |
| 3,888,416 | 6/1975 | Lin | 239/34 |
| 4,017,030 | 4/1977 | Coplan et al. | 222/187 X |
| 4,082,467 | 4/1978 | Kaplan | 401/199 |
| 4,302,899 | 12/1981 | DeHart | 43/1 |
| 4,374,571 | 2/1983 | Hirvela | 239/56 X |
| 4,506,806 | 3/1985 | Lincoln et al. | 222/175 |
| 4,523,717 | 6/1985 | Schwab | 239/56 |

FOREIGN PATENT DOCUMENTS 408186 12/1944 Italy ................................. 401/195

Primary Examiner—Joseph J. Rolla
Assistant Examiner—Kevin P. Shaver
Attorney, Agent, or Firm—Thomas D. Wilhelm

[57] ABSTRACT

The invention is a novel package for dispensing odors such as naturally occurring odors, commonly for the purpose of either masking from wild animals the odor of a human in the vicinity, or for the purpose of attracting wild animals. The package includes a receptacle, a reservoir in the receptacle, and an odor producing liquid in the reservoir. A dispensing conduit extends from the reservoir to a dispensing tip. The microporous construction of the conduit is capable of preferentially absorbing the liquid from the reservoir and conducting it to the tip where it is dispensed by evaporation, or by a touching or rubbing action. A cap is used for closing the package by emplacement over the tip. It is also used for hanging the dispenser. One method of dispensing includes selecting a location, opening the dispenser by removing the cap, and placing the dispensing package in the selected location. Another preferred method includes rubbing the tip on an object, thereby to leave a thin film of the odor producing liquid on the object.

3 Claims, 4 Drawing Figures

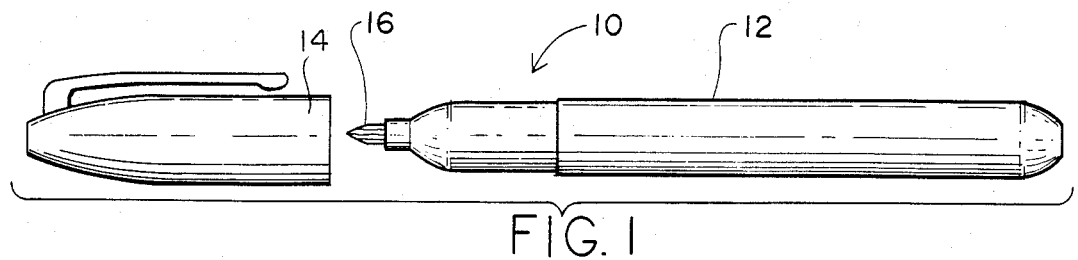
FIG. 1
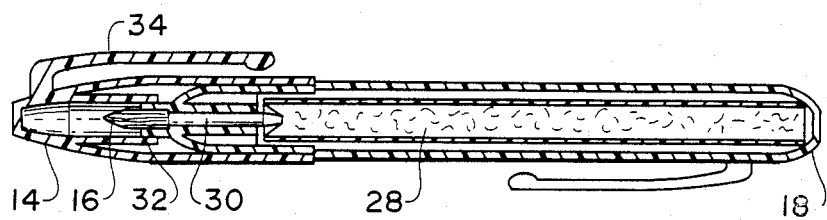
FIG. 2
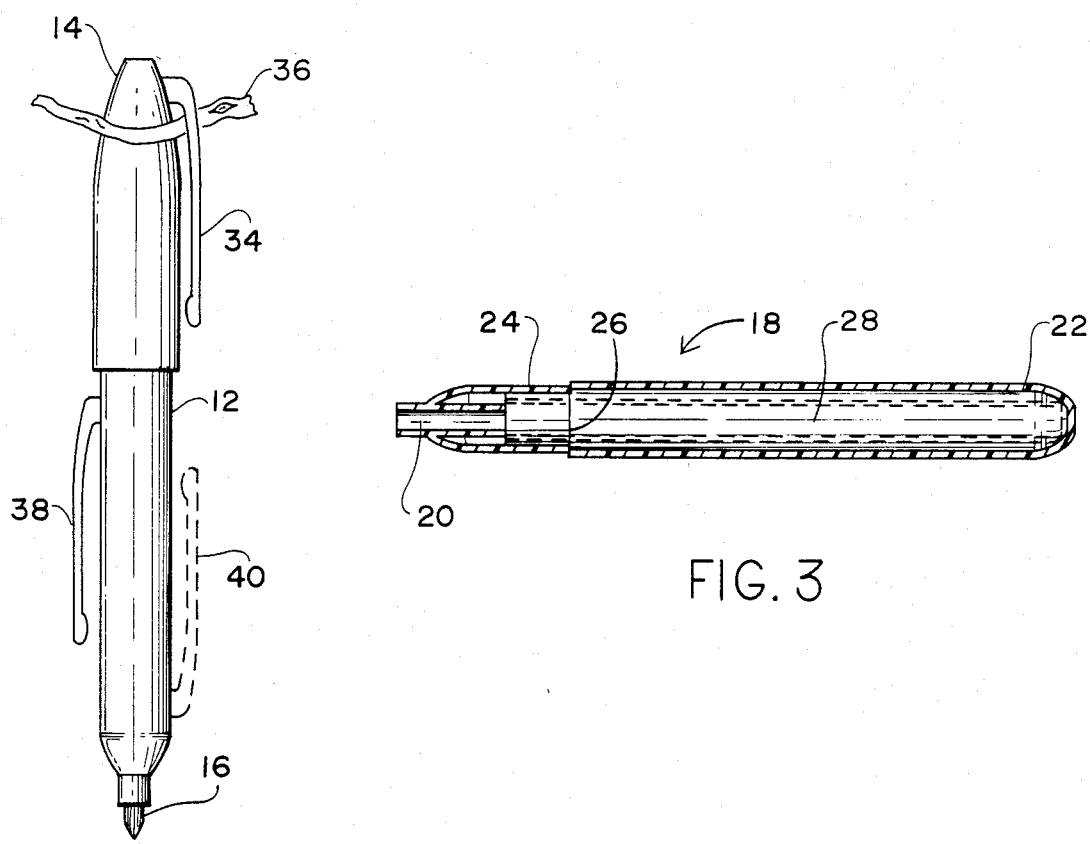
FIG. 3
FIG. 4

DISPENSER AND METHOD FOR DISPENSING HUNTING ODORS

This application is a continuation of application Ser. No. 674,468, filed Nov. 21, 1984, now abandoned, which is a continuation of application Ser. No. 413,080, filed Aug. 30, 1982, now abandoned.

BACKGROUND OF THE INVENTION

This invention pertains generally to the dispensing of hunting odor producing liquids. It is specifically concerned with the dispensing of hunting odors which are intended to create a particular recognition of a naturally occurring odor.

Some odors are used to mask the smell of a human. Particularly strong odors such as the skunk odor work well as masks, although the strength of odor required depends in part on the strength of the odor being emitted by the human, or more particularly the strength of the odor which is to be masked. The dispensed odor, if strong enough, overpowers an animal's odor sensors so that the odor to be masked is not detected.

Another use of dispensed odors in creating recognition in animals is as an attractant. Deer, for example, are attracted to certain natural smells emitted by other deer. A buck deer may be attracted to the natural smell of a doe which is ready for breeding. And does are at times attracted to certain natural smells emitted by a buck.

By proper and clever use of odors to imitate certain natural smells, a person may, at times, be very close indeed to certain animals which are otherwise difficult to approach, without the person ever being detected by smell. And the person may, by the use of odors, attract a larger number of animals to a location, where the person may be. These methods are useful for hunting the larger species of wild game, particularly where it is necessary to come into close proximity to the game. For example, the photographer comes into close proximity to take good photographs. The archer typically comes within at least 25 yards of the animal before attempting to shoot it. And in densely populated areas, where shotguns typically used for hunting, approach to within 75 yards is important, and to within 50 yards is desirable. The animals involved are sometimes able to detect a human odor at much greater distances than these. Thus is the intelligent use of odors helpful in manipulating game into close proximity.

Odor producing products for hunting are most commonly sold as freely flowing liquids in a plastic bottle where the bottle has a cap with a stowable dispensing nozzle built into it. When the nozzle is erected, a hole, of about 1 or 2 millimeters diameter through the nozzle provides a dispensing passage. The liquid is dispensed by turning the bottle upside down and squeezing the bottle to dispense the liquid as drops. Using this technique, the odor producing liquid for hunting may conveniently be emplaced on an absorbent material such as clothing. It is also commonly desirable to emplace the odor producing liquid for hunting on certain non-absorbent objects—namely objects which do not readily absorb liquid. Such objects as boots, belts, trees, leaves, logs and the like are also good places for emplacing a film of the odor producing liquid. This is quite difficult with the dropwise dispensing bottles, as the drops tend to fall off the non-absorbent objects onto the ground and ground litter, where they are not nearly as effective. This is a significant loss of such a costly product. While it is possible to emplace the liquid on non-absorbent articles, it is messy, and wasteful, because of the dripping losses. Regarding absorbent objects, such as the hunter's clothing, some people find the odors which are used to be objectionable, and so are not anxious to put the liquid on their clothing.

Another problem with the capped bottle style container is that the cap itself may loosen, and the contents of the bottle may leak out. This can easily happen as the user may keep the bottle in a pocket while actively engaging in the hunt, and may totally ignore equipments while thusly engrossed in the hunt.

As an attempted improvement on this system, cloth patches have been used, wherein the liquid is put on a small patch of cloth. The cloth is then emplaced. It may be pinned to the user, for example, or emplaced anywhere in the area desired, wherever a stable location may be found, where it will not be blown away, for example. This method is still messy, and other than the use of a pin, no efficient provision has been made for emplacing the patches so they would be stable, and not blown around or otherwise moved from the desired location. Also, temporary storage of the once-used patches may be desirable, but no good storage method has yet been proposed.

While existing products have been used for many years, the above identified needs and problems have not been resolved. Liquid is still being spilled and dripped into the ground. Hunters still mark their own clothing, and tolerate the lingering smell on the clothing after the hunt.

It is a primary object of this invention to provide an improved dispensing package for the containment and dispensing of odor producing liquids for hunting, and improved methods for dispensing the liquid. It is a further object to provide an odor dispensing package which can be readily used to mark non-absorbent objects without dripping substantial portions of the liquid from the object being marked, or unintentionally spilling the liquid from the package. It is still another object to provide a package which can be set up to dispense the liquid at a relatively uniform rate without the risk of spilling the liquid. Another objective is to provide a package which minimizes the risk of liquid spills under all conditions of shipping, handling, and use.

SUMMARY OF THE INVENTION

It has now been found that certain of the foregoing and other objectives are achieved in a hunting odor dispensing package, wherein the hunting odor is identical or similar to a naturally occurring environmental odor. The package includes a receptacle capable of holding a hunting odor producing liquid, with the receptacle having an opening in it for ingress and egress of a liquid product. A reservoir is inside the receptacle. The reservoir is capable of preferentially absorbing and loosely holding liquid when liquid is placed in the receptacle.

The package includes a low viscosity liquid in the receptacle, the liquid being capable of producing a hunting odor which is identical or similar to a naturally occurring environmental odor.

In the receptacle is a dispensing conduit. The conduit is in intimate contact with the reservoir and extends from the reservoir to a dispensing tip outside the receptacle. The conduit has a microporous construction which is capable of absorbing low viscosity liquid from the reservoir and conducting it to the tip. The tip is adapted for dispensing the liquid by evaporation of the liquid from the tip, or applying liquid to an object by rubbing the tip on the object. Finally the package has a cap, which, when placed on the package to close it, is substantially capable of preventing the emission of the odorous vapors. In a preferred package, the receptacle is cylindrical and the cap can be friction fitted on an end of the receptacle opposite the opening. The cap includes means for hanging the package when the cap is fitted on the recited end, and the hanging means is operative for hanging the package with the tip pointed downwardly. Commonly the hanging means is a clip such as like a pocket clip commonly used on pens and pencils.

In some embodiments, the receptacle has a means for hanging the package. There may be hanging means operative for hanging the package with the tip pointed downwardly for a rapid dispensing rate. There may be hanging means operative for hanging the package with the tip pointed upwardly for a slower dispensing rate.

In preferred packages, the major proportion of the odor producing components of the liquid is naturally occurring.

The invention includes a method of dispensing the odor in hunting using the above described package, with the steps of selecting a location for dispensing the odor, removing the cap from the dispenser, and emplacing the dispensing package in the selected location. The odor producing liquid is emitted by evaporation from the tip, and the conduit is effective to draw a supply of liquid to the tip until either the cap is replaced or the liquid is effectively all emitted.

A preferred method of emplacing the package is by hanging it. Depending on the dispensing rate desired, the dispenser may be emplaced with the tip disposed upwardly, for slow dispensing, or downwardly for faster dispensing. For maximum dispensing rate, the method includes the step of shaking the dispenser. The proper shaking is that which generates centrifugal force for forcing an extra supply of the liquid to the tip.

In an especially preferred method of dispensing, the tip is touched to an object, or rubbed across it, thereby transferring some of the odor producing liquid to the object. The odor producing liquid is then emitted into the air by evaporation of the liquid from the object.

BRIEF DESCRIPTION OF THE DRAWINGS

FIG. 1 is a pictorial view of a dispenser of this invention, showing the cap removed.

FIG. 2 is a cross-section of a dispenser of this invention, with the cap fitted tightly on the dispenser.

FIG. 3 shows a cross-section of a receptacle useful in the dispenser of the invention, with a reservoir shown in phantom outline.

FIG. 4 shows the dispenser hanging with the tip down.

DETAILED DESCRIPTION OF THE PREFERRED EMBODIMENT

The invention will now be described in detail in relation to the drawings. FIG. 1 shows a dispenser generally designated as 10. The dispenser is comprised generally of a body portion 12 and a cap 14. On one end of the body portion 12 is a dispensing tip 16, with the tip, body and cap so cooperatively sized that the cap fits closely over the projecting end of the body to close the dispenser and thereby prevent dispensing when dispensing is not desired.

FIG. 2 shows the internal construction of the dispenser in detail. The outer shell of body portion 12 is a receptacle 18 of generally cylindrical shape as shown in cross-section in FIGS. 2 and 3. The receptacle 18 has an opening 20 at one end, while the other end is closed. Normally the receptacle is molded using conventional plastic molding techniques. It has a lower body portion 22 and an upper body portion 24, the upper and lower body portions being joined at a joint line 26.

Returning now to FIG. 2, there is seen a reservoir 28 and a dispensing conduit 30 which connects to tip 16. The cap 14 fits snugly over the upper body portion 24. An internal cap projection 32 extends from the closed end of the cap up to and over the opening 20 of the upper body portion of the receptacle. Projection 32 fits snugly over the receptacle portion of opening 20, thus enclosing tip 16 in the small enclosure created by projection 32 and the end of the cap. This provides a kind of double seal, including the interior projection 32 and the outer body portion of cap 14, with the double seal being beneficial in minimizing uncontrolled emission of odors from the dispenser. While the dispenser is very efficient when used and needed, the odor producing liquids packaged therein may be undesirable for continuous smelling. Further, the undesired emission of odors is wasteful of their intended use.

The dispenser of this invention is intended for dispensing low-viscosity hunting odor producing liquids, where the viscosity is generally similar to that of water. Receptacle 18 is typically made of two pieces of molded plastic, lower body portion 22 and upper body portion 24. As best seen in FIG. 3, the upper and lower body portions are joined at a joint line 26, typically by welding. With the exception of opening 20, after the upper and lower body portions are joined, receptacle 18 is then impervious to the passage of watery liquids, and thus it will serve well as a container of liquids.

In the receptacle is a reservoir 28. The purpose of reservoir 28 is to absorb, hold and retain liquid which is placed in the receptacle. As seen in FIG. 2, the reservoir generally fills the receptacle cavity. The nature of the preferred version of the reservoir is that of loosely packaged fibers contained in a cylindrical wrapping of plastic. The loosely packaged fibers are so spaced that liquid is preferentially drawn by capillary action into the reservoir when liquid is placed in the receptacle. Preferrably the fiber spacing is relatively loose, the fibers being just close enough together to assure that capillary-type attraction holds a volume of liquid in the reservoir. Thus the reservoir is a means of positioning the liquid product, so that it doesn't slosh around in the receptacle body, and so that it is assuredly positioned for presentation to a dispensing conduit.

On one end of the reservoir, dispensing conduit 30 is in intimate contact with, and as shown in FIG. 2, may be depressed into, reservoir 28. The conduit 30 extends out opening 20 and terminates in tip 16. While the conduit 30 and tip 16 are separately iterated for clarity of function, the combination is preferably a continuous and unitary element of the dispenser. Alternately, the conduit and tip may be separate elements which cooperate to support the dispensing function.

In order for conduit 30 to function most efficiently in conducting hunting odor producing liquid to tip 16, the liquid must be preferentially attracted to the material of conduit 30 and tip 16. This is accomplished by selecting the materials of reservoir 28 and the conduit-tip element for cooperative capillary-type action. In reservoir 28, the fibers are loosely packed together to loosely hold the bulk of the liquid.

The construction of the tip and conduit element functions as closely spaced fibrous capillaries, extending from the free end of the conduit to the tip. The closely spaced capillaries, by the physical laws of capillary action, preferentially draw the liquid away from the reservoir and toward the tip, retaining a preferrential relative saturation in the conduit and tip at the expense of saturation of reservoir 28, as applicable.

With the cap removed, as in FIG. 4, liquid at the tip 16 evaporates, creating a capillary action to draw replacement liquid to the tip. In like manner, liquid is continuously drawn to the tip as long as the cap is left off. As the supply of liquid in reservoir 28 becomes depleted, the maximum rate at which the remaining liquid can be transported to the tip decreases until it reaches unacceptably low levels. At that point the remaining liquid in the dispenser is considered not dispensable, since effective dispensing is no longer being achieved.

Hunting odor producing liquids useful in this invention include those which are naturally occurring in the environment, or are similar to naturally occurring odors. Those commonly in use are typically representative of either certain animal odors or the odors of certain foods of animals. Examples of odors useful in this invention are those of musk, doe in heat, pine, cedar, apple, earth, acorn, deer glands, raccoon, pheasant, quail, rabbit, corn, and grape. Those skilled in the art will appreciate that this listing is exemplary only, and is not exhaustive of the useful naturally-occurring odors.

In assembling the dispensing package of the invention, a reservoir 28 is first placed in lower body portion 22. Upper body portion 24 is then placed over lower body portion 22 and the two are joined together as at joint line 26. At this point the package looks like the representation of FIG. 3, wherein the included reservoir is shown in phantom outline. The next operation is the filling of the receptacle and reservoir with liquid. After liquid filling, the conduit-tip element is pressed into place and the cap pressed on. That completes the assembly operation of the preferred embodiment, with the finally assembled package being represented by FIG. 2.

Dispensing of the liquid for hunting purposes is very simple, although a variety of dispensing methods is available. The easiest method, and an effective one is to simply remove the cap, place it over the closed end of the receptacle 18 and hang the assembly up by the clip 34 which is molded integrally into the cap, all as seen in FIG. 4. In that position, the dispensing is by evaporation from the tip. Liquid is moved toward the tip 16 by a combination of the forces of capillary action and gravity. In alternate construction, the dispenser may be hung by clips attached to the receptacle 18. Illustrative is clip 38 for hanging with the tip down.

Shown in phantom, is another clip arrangement 40 for hanging with the tip pointed up. For slower dispensing, the tip-up orientation is preferred. In this case, the forces of capillary action are the same, but the gravitational forces are now working against transport of the liquid.

A critical feature of the invention is that, as liquid is removed from the tip, by evaporative emission or by marking an object, such as by touching or rubbing it with the tip, additional liquid is drawn to the tip by capillary action, providing a constant supply of liquid at the exterior surface of the tip. For evaporative emission, this constant supply yields a relatively constant emission rate.

A feature of the invention which has long been urgently needed is the ability to easily and efficiently mark objects so that they emit the desired odor. In doing this, the tip is merely touched to the surface of the object, or rubbed across it. Liquid at the tip is left on the object in a thin layer, or film. Even non-absorbent objects, such as equipment, boots, belts, leaves, logs, tree branches and the like may be thus marked.

With the liquid being dispensed by means of the microporous tip, the user can easily place odor-emitting marks on several objects if desired. In doing so, the film left by the dispenser is thin enough that there is no risk of loss by dripping off the object. Similarly, there is likewise no risk of unintentionally dripping liquid from the dispenser, since the microporous tip efficiently retains the liquid for dispensing, and the liquid is not subject to otherwise getting out of the package. Once desired objects have been marked, the dispenser itself may be used as an emitter by locating it as desired with the cap removed from the tip. The dispenser may be hung from an object, such as a branch 36 as shown in FIG. 4. Alternately, the closed end of the receptacle 18 may be forced into soft ground with the tip disposed upwardly for dispensing. A clever user will, of course, improvise other dispenser holders to fit the situation.

Thus it is seen that the novel dispenser of this invention can dispense odor producing liquids efficiently in a variety of modes, without risk of dripping the liquid or having the liquid unintentionally drain from the dispensing container. Objects may be easily marked with the liquid. The dispenser itself may be used as an emitter of the hunting odor producing liquid. In that role, the rate of emission may be partially controlled by pointing the tip down for more rapid emission, or pointing it up for slower emission. Thus is the user provided with a versatile, efficient dispenser for a product which has been in general use, with other dispenser-containers, for many years.

Clearly the shape of the packaging dispenser of this invention may be altered as convenient so long as the basic functional characteristics are preserved.

Having thus described the invention, what is claimed is:

1. A hunting odor package and dispenser, comprising:
   (a) a container, including (i) a receptacle capable of holding a hunting odor producing liquid, (ii) a reservoir inside said receptacle for absorbing and holding a hunting odor producing liquid, (iii) a conduit and a dispensing tip, said conduit being in intimate contact with said reservoir and extending from said reservoir to said tip, and (iv) a cap; and
   (b) a low viscosity hunting odor producing liquid in said receptacle.

2. A method of dispensing a hunting odor from an odor dispensing package, said method comprising the steps of:
   (a) packaging a hunting color producing liquid in a receptacle, said receptacle being capable of holding said liquid, said package having (i) in said receptacle, a reservoir capable of absorbing and holding said liquid; (ii) a dispensing conduit and a dispensing tip, said conduit being in intimate contact with said reservoir and extending from said reservoir to said tip; and (iii) a cap;

(b) selecting a hunting location for dispensing said hunting odor;
(c) removing said cap from said dispensing package; and
(d) emplacing said hunting odor dispensing package in the selected location;
whereby said hunting odor producing liquid is caused to be emitted from said tip.

3. A method of dispensing a hunting odor from an odor producing package, said method comprising the steps of:
(a) packaging a hunting odor producing liquid in a receptacle, said receptacle being capable of holding said liquid, said package having (i) in said receptacle, a reservoir capable of absorbing and holding said liquid, (ii) a dispensing conduit and a dispensing tip, said conduit being in intimate contact with said reservoir and extending from said reservoir to said tip, and (iii) a cap;
(b) selecting a hunting location for dispensing said hunting odor; and
(c) touching said tip to an object at said location, thereby transferring a small amount of said hunting odor producing liquid to said object, whereby said hunding odor producing liquid is emitted by evaporation from said object to produce a hunting odor.

* * * * *